United States Patent [19]
Evers et al.

[11] 3,933,863
[45] Jan. 20, 1976

[54] 3-FURYL CHALCOGEN ALKYL SULFIDES

[75] Inventors: William J. Evers, Middletown; Igor A. Pelse, Long Branch; Manfred Hugo Vock, Locust, all of N.J.

[73] Assignee: International Flavors & Fragrances Inc., New York, N.Y.

[22] Filed: Jan. 21, 1975

[21] Appl. No.: 542,830

[52] U.S. Cl.............................. 260/347.2; 426/65
[51] Int. Cl.².................................. C07D 307/64
[58] Field of Search................................ 260/347.2

[56] References Cited
OTHER PUBLICATIONS
Weissburger, Heterocyclic Compounds with Three–or Four–Membered Rings, Part One, pp. 331–341 & 604–607 (1964).

*Primary Examiner*—Harry I. Moatz
*Attorney, Agent, or Firm*—Arthur L. Liberman, Esq.; Harold Haidt, Esq.

[57] ABSTRACT

3-Furyl beta-chalcogenalkyl sulfides having the structure:

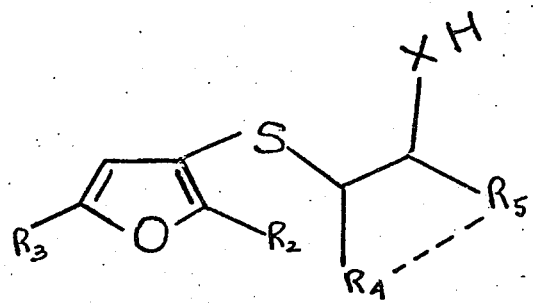

wherein X is a chalcogen selected from the group consisting of oxygen and sulfur; $R_2$ and $R_3$ are each selected from the group consisting of methyl and hydrogen, at least one of $R_2$ or $R_3$ being methyl; and $R_4$ and $R_5$, taken separately, are each methyl, or $R_4$ and $R_5$ taken together are tetramethylene, such 3-furyl beta-chalcogenalkyl sulfides being useful in altering the organoleptic properties of foodstuffs, and processes for producing these 3-furyl beta-chalcogenalkyl sulfides using the reaction:

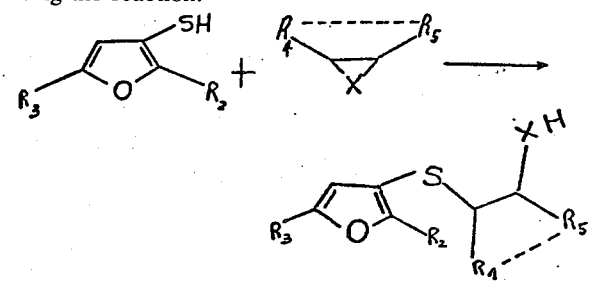

7 Claims, No Drawings

3-FURYL CHALCOGEN ALKYL SULFIDES

BACKGROUND OF THE INVENTION

The present invention relates to novel 3-furyl beta-chalcogenalkyl sulfides.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainity as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is noteable in products having sweet, meaty and roasted meat flavor and nut-like flavor characteristics. It is also noteable in products having vegetable-like and hydrolyzed vegetable protein-like and anise-like flavor characteristics.

Reproduction of roasted, nutty and sweet, meaty flavors and aromas and hydrolyzed vegetable protein-like flavors and aromas has been the subject of the long and continuing search by those engaged in the production of foodstuffs. The severe shortage of foods, especially protein foods, in many parts of the world has given rise to the need for utilizing non-meat sources of proteins and making such proteins as palatable and as meat-like as possible. Hence, materials which will closely simulate or exactly reproduce the flavor and aroma of roasted meat and sweet, meat products, vegetable products and products having nut-like taste are required.

Moreover, there are a great many meat containing or meat based foods presently distributed in a preserved form. Examples being condensed soups, dry-soup mixes, dry meat, freeze-dried or lyophilized meats, packages gravies and the like. While these products contain meat or meat extracts, the fragrance, taste and other organoleptic factors are very often impaired by the processing operation and it is desirable to supplement or enhance the flavors of these preserved foods with versatile materials which have either roasted meat or sweet meat or vegetable-like or nut-like nuances.

U.S. Pat. No. 3,666,594 provided materials having such desirable meat, roast meat and roasted fragrance and flavor notes. Such materials are organic oxygen containing heterocyclics wherein the second carbon atom from the oxygen atom contains a sulfur substituent and included 3-thia furan compounds having the structure:

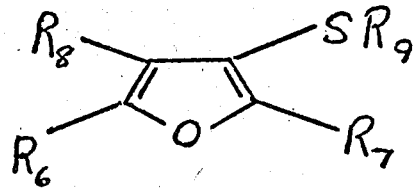

wherein $R_6$, $R_7$, $R_8$ and $R_9$ are the same or different alkyl or hydrogen. The process disclosed in this patent indicated that such furan 3-thiols and alkyl substituted furan 3-thiols can be produced by the reaction of an appropriate dihydro furanone-3-or tetrahydro furanone-3-with hydrogen sulfide in the presence of anhydrous hydrogen chloride at temperatures of −60°C to −100°C.

Nothing in the prior art, however, sets forth implicityly or explicityly the 3-furyl beta-chalcogenalkyl sulfides of our invention and their unique and advantageous and unobvious flavor properties.

Loutham, U.S. Pat. No. 3,384,671 issued on May 21, 1968 discloses a process for the preparation of dithiols by means of the following reaction:

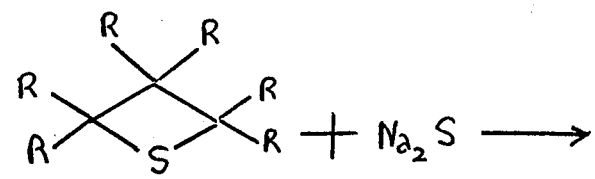

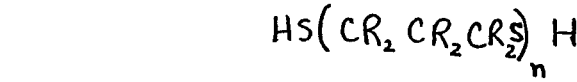

wherein R may be, interalia, hydrogen or alkyl and $n$ is from 3 up to 15.

The use of triethylamine in a reaction of $H_2S$ with 1,2-epoxides (e.g., 1,2-epoxypropane) to form hydroxyalkylmercaptans is disclosed in Jones, U.S. Pat. No. 3,394,192 issued on July 23, 1968.

Neither the Loutham reference nor the Jones reference discloses a process for preparing compounds analogous to the 3-furyl beta-chalcogenalkyl sulfides of our invention.

The present invention provides novel 3-furyl beta-chalcogenalkyl sulfides useful for altering the organoleptic properties of foodstuffs, a novel process for producing said 3-furyl beta-chalcogenalkyl sulfides as well as methods for altering the organoleptic properties of said foodstuffs.

The novel compounds are 3-furyl beta-chalcogenalkyl sulfides having the structure:

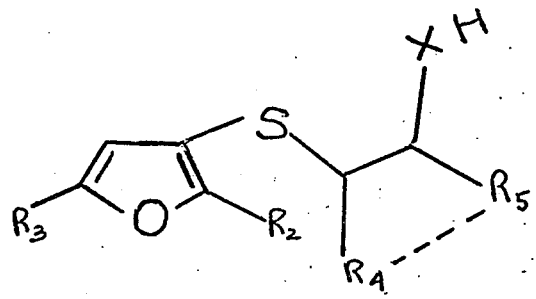

wherein X is a chalcogen selected from the group consisting of oxygen and sulfur; $R_2$ and $R_3$ are each selected from the group consisting of methyl and hydrogen, at least one of $R_2$ or $R_3$ being methyl; and $R_4$ and $R_5$, taken separately, are each methyl, or $R_4$ and $R_5$ taken together are tetramethylene.

Thus, 3-furyl beta-chalcogenalkyl sulfides contemplated within the scope of our invention are, for example:

The 3-furyl beta-chalcogenalkyl sulfides of our invention may be produced according to a process which comprises the steps of:

i. Carrying out a reaction of a 3-mercapto furan with a thiirane or epoxide to form the compounds of our invention according to the following reaction:

| 3-Furyl Beta-Chalcogenalkyl Sulfide Compound | Structure |
|---|---|
| (2,5-dimethyl-3-furyl)(2-mercapto-1-methyl propyl) sulfide | 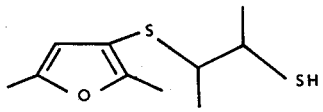 |
| (2,5-dimethyl-3-furyl)(2-hydroxy-1-methyl propyl) sulfide | 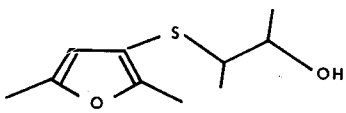 |
| (2-mercapto-1-methyl propyl)(2-methyl-3-furyl) sulfide | 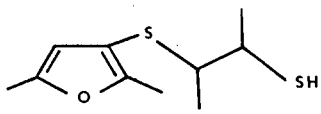 |
| (2-hydroxy-methyl propyl)(2-methyl-3-furyl) sulfide | 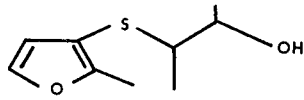 |
| (2-hydroxy cyclohexyl)(2-methyl-3-furyl) sulfide | 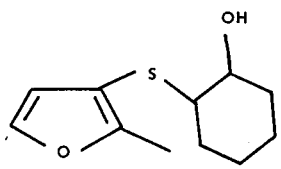 |
| (2,5-dimethyl-3-furyl)(2-hydroxy cyclohexyl) sulfide | 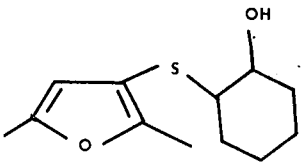 |

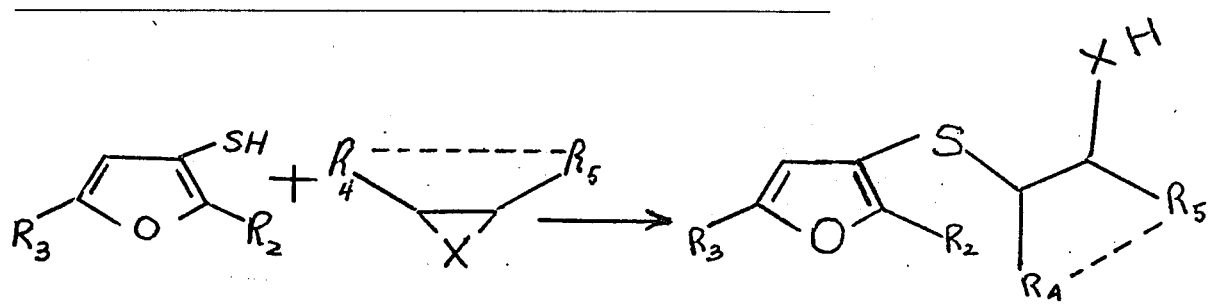

ii. Physically separating said 3-furyl beta-chalcogenalkyl sulfides from the reaction mass, wherein X, $R_2$ and $R_3$ are defined as above.

The following table sets forth examples of specific reactants and the resulting products produced using the process of our invention:

TABLE I

| Thiirane or Epoxide Reactant | 3-Furan Thiol Reactant | 3-Furyl β-Chalcogenalkyl Sulfide Reaction Product | Structure |
| --- | --- | --- | --- |
| 2,3-epithiobutane | 2,5-dimethyl-3-furan thiol | (2,5-dimethyl-3-furyl) (2-mercapto-1-methyl propyl) sulfide | |
| 2,3-epoxybutane | 2,5-dimethyl-3-furan thiol | (2,5-dimethyl-3-furyl) (2-hydroxy-1-methyl propyl) sulfide | |
| 2,3-epithiobutane | 2-methyl-3-furan thiol | (2-mercapto-1-methyl propyl) (2-methyl-3-furyl) sulfide | |
| 2,3-epoxybutane | 2-methyl-3-furan thiol | (2-hydroxy-1-methyl propyl) (2-methyl-3-furyl) sulfide | |
| 2,3-epithiobutane | 5-methyl-3-furan thiol | (2-mercapto-1-methyl propyl) (5-methyl-3-furyl) sulfide | |
| 2,3-epoxybutane | 5-methyl-3-furan thiol | (2-hydroxy-1-methyl propyl) (5-methyl-3-furyl) sulfide | |
| 1,2-epoxycyclohexane | 2-methyl-3-furan thiol | (2-hydroxy cyclohexyl) (2-methyl-3-furyl) sulfide | |
| 1,2-epoxycyclohexane | 2,5-dimethyl-3-furan thiol | (2,5-dimethyl-3-furyl) (2-hydrocyclohexyl) sulfide | |

The reaction of our invention, in order to proceed in a practical manner, should take place in the presence of a basic catalyst, preferably a lower alkyl amine such as diethyl amine, triethyl amine or trimethyl amine.

The reaction is also best carried out in the presence of a non-reactive solvent such as a lower alkanol, preferably methanol, ethanol or n-propanol.

The mole ratio of reactants, the 3-furan thiol: the epoxide or thiirane may vary from 1:1 to 5:1 with a preferred ratio of 3-furan thiol:epoxide or thiirane of 2:1.

The reaction temperature may vary from 50°C up to 80°C, the time of reaction being a function of the reaction temperature, with lower reaction temperatures giving rise to longer periods of time of reaction and higher temperatures of reaction giving rise to much shorter periods of time of reaction. Thus, for example, it is preferred to run the reaction for optimum yield at a temperature in the range of 50°–65°C for a period of time for approximately 45 minutes.

The reaction is preferably carried out at atmospheric pressure but pressures greater than atmospheric, e.g., 5 atmospheres may be used without detrimentally affecting the yield of product of the time of reaction which is required to attain such yield.

At the end of the reaction, the reaction product is extracted from the reaction mass using a nonreactive solvent, e.g., methylene dichloride, after the reaction mass is first quenched with water and neutralized with aqueous acid. The solvent extract is then dried, concentrated and distilled preferably by means of vacuum distillation.

The following reactions are illustrative of the process of our invention:

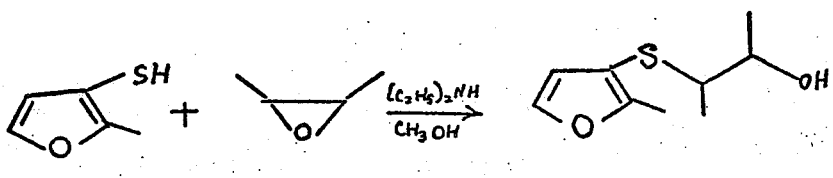

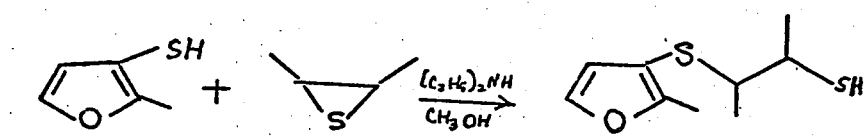

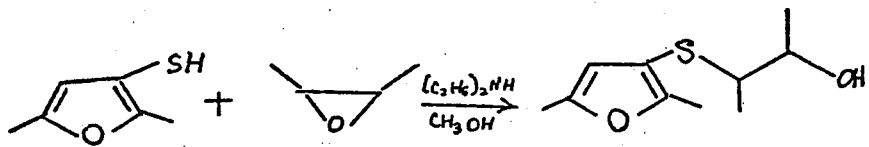

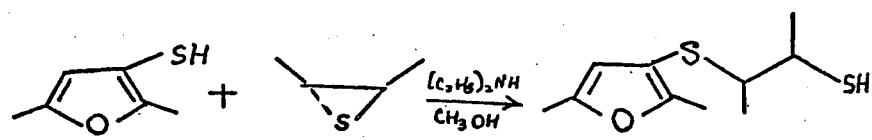

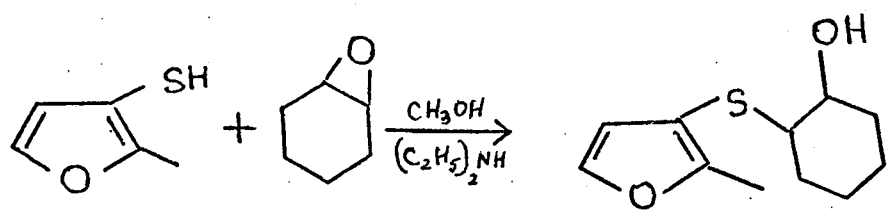

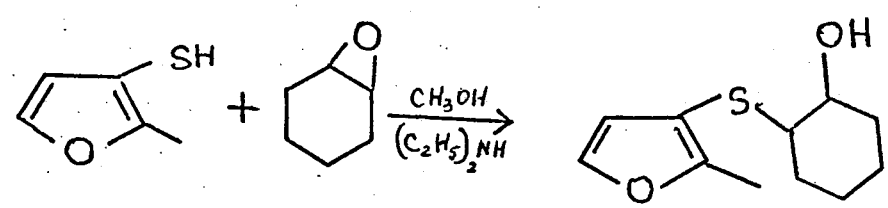

The 3-furyl beta-chalcogenalkyl sulfides of our invention produced in this manner have useful organoleptic properties giving rise to their use as foodstuff flavors as set forth in an illustrative manner in the following table:

TABLE II

| 3-Furyl β-Chalcogenalkyl Sulfide Compound | Structure | Flavor Properties |
| --- | --- | --- |
| (2,5-dimethyl-3-furyl) (2-mercapto-1-methyl propyl) sulfide | 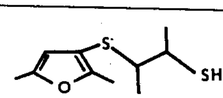 | Sweet, meaty, nutty aroma and a "turkey aroma nuance" and a sweet, meaty, nutty flavor with pecan, turkey, Brazil nut and bitter nuances. |
| (2,5-dimethyl-3-furyl) (2-hydroxy-1-methyl propyl) sulfide | 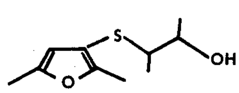 | Nutty, meaty aroma and a nutty, pot roast, hydrolyzed vegetable protein flavor with metallic and bitter nuances. |
| (2-mercapto-1-methyl propyl (2-methyl-3-furyl)sulfide | 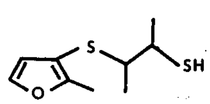 | Nutty, turkey aroma and a roast turkey, Brazil nut and roasted hazlenut flavor with |

TABLE II-continued

| 3-Furyl β-Chalcogenalkyl Sulfide Compound | Structure | Flavor Properties |
|---|---|---|
| | | metallic, bitter nuances. |
| (2-hydroxy-1-methyl propyl) (2-methyl-3-furyl)sulfide | 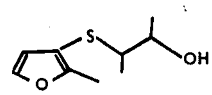 | Sweet, hydrolyzed vegetable protein and gravy aroma and sweet, mouth feel and roasted meat flavor with hydrolyzed vegetable protein, meat extract, walnut and pecan nuances. |
| (2-hydroxycyclohexyl) (2-methyl-3-furyl) sulfide | 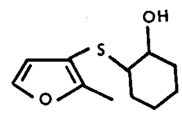 | Pork, meaty, sweet aroma with nutty and bacon rind nuances and a sweet, meaty, pork flavor with bacon rind, nutty and mouth-feel nuances. |
| (2,5-dimethyl-3-furyl) (2-hydrocyclohexyl) sulfide | 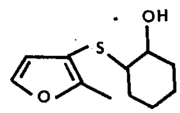 | Sweet, meaty, nutty aroma with pork and yeasty nuances and a sweet and meaty flavor with pork, yeasty and mouth-feel nuances. |

Thus, the 3-furyl beta-chalcogenalkyl sulfides according to the present invention can be used to alter, vary fortify, modify, enhance or otherwise improve the organoleptic properties, including flavor and/or aroma, of a wide variety of materials which are ingested, consumed, or otherwise organoleptically sensed.

The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

Such 3-furan beta-chalcogenalkyl sulfides are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the 3-furan beta-chalcogenalkyl sulfides according to this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surfact active agents, conditioners and flavor intensifiers.

Examples of preferred co-flavoring adjuvants are:
Methyl thiazole alcohol (4-methyl-5-betahydroxyethyl thiazole);
2-Methyl butanethiol;
4-Mercapto-2-butanone;
3-Mercapto-4-pentanone;
1-Mercapto-2-propanone;
Benzaldehyde;
Furfural;
Furfural alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Sulfur-containing amino acids;
Cysteine;
Hydrolyzed vegetable protein;

2-Methylfuran-3-thiol;
2-Methyldihydrofuran-3-thiol;
2,5-Dimethylfuran-3-thiol;
Hydrolyzed fish protein; and
Tetramethyl pyrazine The 3-furyl beta-chalcogenalkyl sulfides or the compositions incorporating them, as mentioned above, can be combined with one or more vehicles or carriers for adding them to the particular product. Vehicles can be edible or otherwise suitable materials such as ethyl alcohol propylene glycol, water and the like. Carriers include materials such as gum arabic, carrageenan, other gums and the like. The 3-furyl beta-chalcogenalkyl sulfides according to this invention can be incorporated with the carriers by conventional means such as spray-drying, drum-drying and the like. Such carriers can also include materials for coacervating the 3-furyl beta-chalcogenalkyl sulfides (and other flavoring ingredients, as present) to provide encapsulated products. When the carrier in an emulsion the flavoring composition can also contain emulsifiers such as mon- and diglycerides or fatty acids and the like. With these carriers or vehicles, the desired physical form of the composition can be prepared.

The quantity of 3-furyl beta-chalcogenalkyl sulfides utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage; if any, to which the product will be subjected; and the preconsumption treatment, such as baking, frying, and so on, given to the product by the ultimate consumer. Accordingly, the terminology "effective amount" and "sufficient amoung" is understood in the context of the present invention to be quantitatively adequate to alter the flavor of the foodstuff.

It is accordingly preferred that the ultimate compositions contain from about 0.02 parts per million (ppm) to about 250 ppm of 3-furyl beta-chalcogenalkyl sulfides or mixtures thereof. More particularly, in food compositions it is desirable to use from about 0.03 ppm to 100 ppm for enhancing flavors and in certain preferred embodiments of the invention, from about 0.05 to 50 ppm of the derivatives are included to add positive flavors to the finished product.

The amount of 3-furyl beta-chalcogenalkyl sulfides or mixtures thereof of our invention to be utilized in flavoring compositions can be varied over a wide range depending upon the particular quality to be added to the foodstuff. Thus, amounts of one or more derivatives according to the present invention of from about 0.5 ppm up to 80 or 90 percent of the total flavoring composition can be incorporated in such compositions. It is generally found to be desirable to include from about 1 ppm up to about 0.1 percent of the 3-furyl beta-chalcogenalkyl sulfides in such compositions.

The following examples are given to illustrate embodiments of the invention as it is preferably preferred to practice it. It will be understood that these examples are illustrative and the invention is not to be considered as restricted thereto except as indicated in the appended claims.

All parts, proportions, percentages, and ratios herein are by weight unless otherwise indicated.

EXAMPLE I

Preparation of (2,5-Dimethyl-3Furyl) (2-Mercapto-1-Methyl Propyl) Sulfide

Reaction:

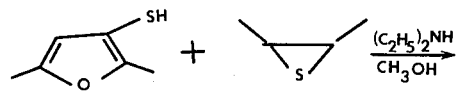

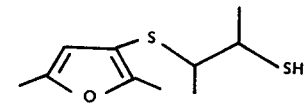

Into a 50 ml 3-neck flask equipped with thermometer, reflux condenser, magnetic stirrer and heating mantle, are charged 1.28 g (.01 moles) 2,5-dimethyl-3-furanthiol, 15 ml of methyl alcohol and 5 drops of diethyl amine.

While the reaction mass is stirred, it is heated to 46°C and 0.44 g (0.005 moles) of 2,3-epithio butane having the structure:

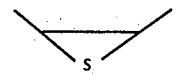

is added to the mass. The reaction mass is then heated to a temperature in the range of 55°–61°C and maintained at that temperature for a period of 45 minutes.

The reaction mass is then poured into water and neutralized with 10% aqueous hydrochloric acid. The resulting mixture is then extracted with methylene dichloride and the resulting extract is dried over anhydrous sodium sulfate and concentrated to an orange oil. The resulting mixture is separated into its components using GLC apparatus (Conditions: 8 feet × ¼ inch 25% SE-30 column; 120°C programmed at 6°C/min). at 6°C/min).

Mass spectral, infra red and NMR analyses confirm the structure as being:

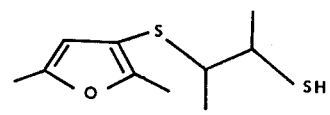

Mass spectral analysis is as follows:
m/e
216 parent ion
128
43
55
89
95
155

This material has a sweet, meaty, nutty aroma and a "turkey aroma nuance" and a sweet, meaty, nutty flavor with pecan, turkey, Brazil nut and bitter nuances.

EXAMPLE II

Preparation of (2,5-Dimethyl-3-Furyl) (2-Hydroxy-1-Methyl Propyl) Sulfide

Reaction:

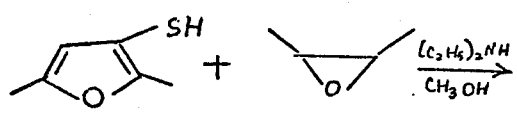

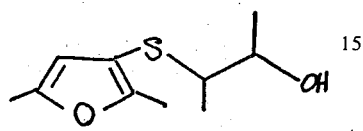

Into a 50 ml 3-neck flask equipped with thermometer, reflux condenser, magnetic stirrer and heating mantle are charged 1.28 g (.01 moles) 2,5-dimethyl-3-furanthiol, 15 ml of methyl alcohol and 5 drops of diethyl amine.

While the reaction mass is stirred, it is heated to 56°C and 0.36 g (0.005 moles) of 2,3 epoxy butane having the structure:

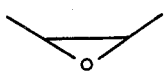

is added to the mass. The reaction mass is then heated to a temperature in the range of 56°–63°C and maintained at that temperature for a period of 45 minutes.

The reaction mass is then poured into water and neutralized with 10% aqueous hydrochloric acid. The resulting mixture is then extracted with methylene dichloride and the resulting extract is dried over anhydrous sodium sulfate and concentrated to an orange oil. The resulting mixture is separated into its components using GLC apparatus (Conditions: 8 feet × ¼ inch 25% SE-30 column; 120°C programmed at 6°C/min).

Mass spectral, infra red and NMR analyses confirm the structure as being:

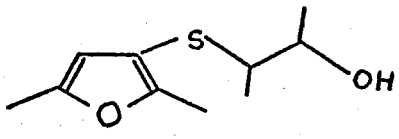

Mass spectral analysis is as follows:
m/e
200 parent ion
43
128
155
95
55
59
113

This material has a nutty, meaty aroma and a nutty, pot roast, hydrolyzed vegetable protein flavor with metallic and bitter nuances.

EXAMPLE III

Preparation of (2-Mercapto-1-Methyl Propyl) (2-Methyl-3-Furyl) Sulfide

Reaction:

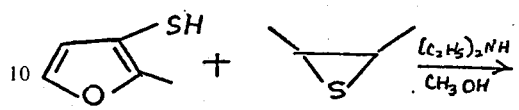

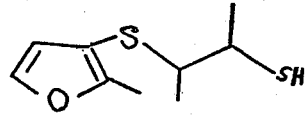

Into a 50 ml 3-neck flask equipped with thermometer, reflux condenser, magnetic stirred and heating mantle are charged 1.14 g 2-methyl-3-furanthiol, 15 ml of methyl alcohol and 5drops of diethyl amine.

While the reaction mass is stirred, it is heated to 50°C and 0.44 g (0.005 moles) of 2,3-epithio butane having the structure;

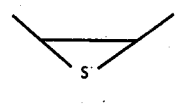

is added to the mass. The reaction mass is then heated to a temperature in the range of 50°–58°C and maintained at that temperature for a period of 90 minutes.

The reaction mass is then poured into water and neutralized with 10% aqueous hydrochloric acid. The resulting mixture is then extracted with methylene dichloride and the resulting extract is dried over anhydrous sodium sulfate and concentrated to an orange oil. The resulting mixture is separated into its components using GLC apparatus (Conditions: 8 feet × ¼ inch 25% SE-30 column; 120°C programmed at 6°C/min).

Mass spectral, infra red and NMR analyses confirm the structure as being:

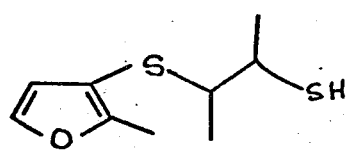

Mass spectral analysis is as follows:
m/e
202 parent ion
114
55
89
43
141

This material has a nutty, turkey aroma and a roast turkey, Brazil nut and roasted hazlenut flavor with metallic, bitter nuances.

EXAMPLE IV

Preparation of (2Hydroxy-1-Methyl Propyl) (2-Methyl-3-Furyl) Sulfide

Reaction:

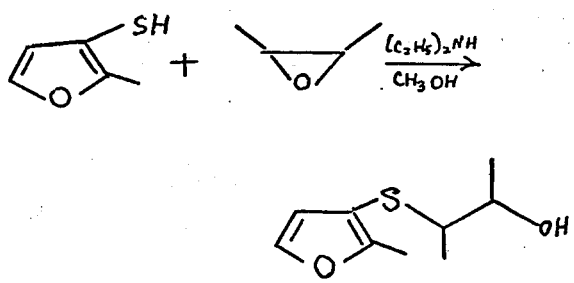

Into a 50 ml 3-neck flask equipped with reflux condenser, magnetic stirrer and heating mantle are charged 1.14 g 2-methyl-3-furanthiol, 15 ml of methyl alcohol and 5 drops of diethyl amine.

While the reaction mass is stirred, it is heated to 50° and 0.36 g of 2,3 epoxy butane having the structure:

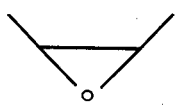

is added to the mass. The reaction mass is then heated to a temperature in the range of 50°–58°C and maintained at that temperature for a period of 80 minutes.

The reaction mass is then poured into water and neutralized with 10% aqueous hydrochloric acid. The resulting mixture is then extracted with methylene dichloride and the resulting extract is dried over anhydrous sodium sulfate and concentrated to an orange oil. The resulting mixture is separated into its components using GLC apparatus (Conditions: 8 feet × ¼ inch 25% SE-30 column; 120°C programmed at 6°C/min).

Mass spectral, infra red and NMR analyses confirm the structure as being:

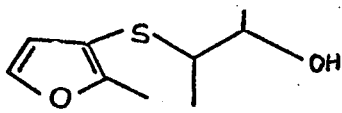

Mass spectral analysis is as follows:
m/e
186 parent ion
114
141
43
55
59
86

This material has a sweet, hydrolyzed vegetable protein and gravy aroma and sweet, mouth feel and roasted meat flavor with hydrolyzed vegetable protein, meat extract, walnut and pecan nuances.

EXAMPLE V (2-Hydroxy-1-methyl propyl) (2-methyl-3-furyl) sulfide prepared according to the process of Example IV is added to a 2% aqueous solution of Wyler's "Beef Flavored Instant Bouillon" (manufactured by Wyler Foods, Division of Borden, Inc., Chicago, Il., U.S.A.).
(Ingredients: salt, hydrolyzed vegetable protein, malto dextrin, sugar, beef fat, water, mono-sodium glutamate, "flavorings", corn sugar, beef extract, caramel color, hydrogenated vegetable fat, U.S. certified food color)

at the rate of 1 ppm. The resulting beef flavor has a sweet, meat extract-like character. The meaty mouth feel is improved and a better after taste is thus achieved.

EXAMPLE VI (2-Mercapto-1-methyl propyl) (2-methyl-3-furyl) sulfide prepared according to the process of Example III is added to a 2% aqueous solution of Wyler's "Beef Flavored Instant Bouillon" (manufactured by Wyler Foods, Division of Borden, Inc., Chicago, Il. U.S.A.).
(Ingredients: salt, hydrolyzed vegetable protein, malto dextrin, sugar, beef fat, water, mono-sodium glutamate, flavorings, corn sugar, beef extract, caramel color, hydrogenated vegetable fat and U.S. certified food color)

at the rate of 1 ppm. The resulting beef broth flavor is substantially improved having a sweet, bloody, metallic, meat like note with a vegetable like aftertaste. Over-all, the resulting beef broth has better meaty characteristics.

EXAMPLE VII (2,5-Dimethyl-3-furyl) (2-hydroxy-1-methyl propyl) sulfide prepared according to the process of Example II is added to a 2% solution of Wyler's "Beef Flavored Instant Bouillon" (manufactured by Wyler Foods, Division of Borden, Inc., Chicago, Il. U.S.A.).
(Ingredients: salt, hydrolyzed vegetable protein, malto dextrin, sugar, beef fat, water, monosodium glutamate, flavorings, corn sugar, beef extract, caramel color, hydrogenated vegetable fat, U.S. certified food color)

at the rate of 2 ppm. The resulting beef broth flavor has a roasted meat character added thereto with the vegetable note depressed and a natural beef broth like after taste added.

EXAMPLE VIII (2,5-Dimethyl-3-furyl) (2-mercapto-1-methyl propyl) sulfide prepared according to the process of Example I is added to a 2% solution of Wyler's "Beef Flavored Instant Bouillon" (manufactured by Wyler Foods, Division of Borden, Inc., Chicago, Illinois, U.S.A.).
(Ingredients: salt, hydrolyzed vegetable protein, malto dextrin, sugar beef fat, water, mono-sodium glutamate, flavorings, corn sugar, beef extract, caramel color, hydrogenated vegetable fat and U.S. certified food color)

at the rate of 1 ppm. This chemical depresses the vegetable notes of the beef broth and improves the meat flavor by adding natural meat like notes.

EXAMPLE IX

The (2,5-dimethyl-3-furyl) (2-mercapto-1-methyl propyl) sulfide prepared in Example I is dissolved in propylene glycol to provide a 0.1% solution. This solution in the amount of 0.9 g is added to 7.3 g of a soup base consisting of:

| Ingredient | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting mixture is added to 12 ounces of boiling water to obtain a soup having a characteristic meat flavor.

EXAMPLE X

The (2,5-dimethyl-3-furyl) (2-hydroxy-1-methyl propyl) sulfide prepared in Example II is dissolved in propylene glycol to provide a 0.1% solution. This solution in the amount of 0.9 g is added to 7.3 g of a soup base consisting of:

| Ingredient | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting mixture is added to 12 ounces of boiling water to obtain a soup having an excellent meat flavor.

EXAMPLE XI

50:50 Mixture of (2-mercapto-1-methyl propyl) (2-methyl-3-furyl) sulfide and (2-hydroxy-1-methyl propyl) (2-methyl-3-furyl) sulfide prepared in Examples III and IV is dissolved in propylene glycol to provide a 0.1% solution. This solution in the amount of 0.9 g is added to 7.3 g of a soup base consisting of:

| Ingredient | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting mixture is added to 12 ounces of boiling water to obtain a soup having an excellent sweet meat flavor.

EXAMPLE XII

Preparation of (2-Hydroxy Cyclohexyl) (2-Methyl-3-Furyl) Sulfide Reaction:

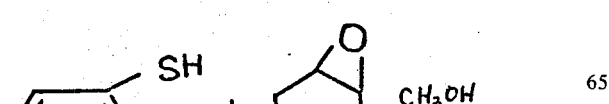

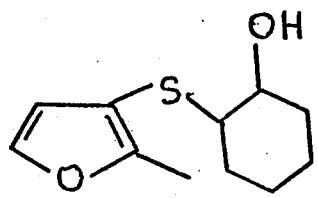

A test tube equipped with a magnetic stirrer is immersed in a water bath. Into the test tube are charged 1 ml of methanol, 4 drops of diethyl amine, 20 drops of 2-methyl-3-furanthiol, and 12 drops of cyclohexene oxide. The reaction mass is heated with stirring on a hot plate at about 60°C for 2 hours. The reaction mass is then concentrated in vacuo on a rotary evaporator. The product is isolated by preparative GLC (Conditions: 8 feet × ¼ inch 25% SE-30 column; 120°C programmed at 6°C/min).

Mass spectral, infrared and NMR analyses confirm the structure as being:

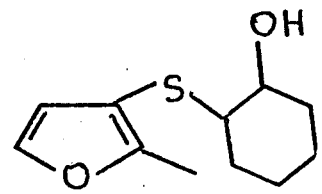

Mass spectral analysis is as follows:

| m/e | |
|---|---|
| 212 parent ion | 43 |
| 114 | 41 |
| 81 | 28 |

This material has a pork, bacon rind character.

EXAMPLE XIII

Preparation of (2,5-Dimethyl-3-Furyl) (2-Hydroxycyclohexyl Sulfide

Reaction:

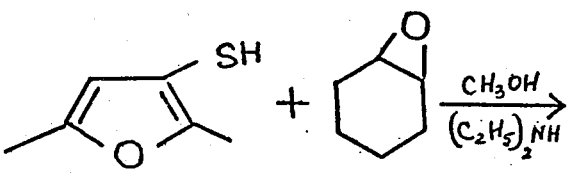

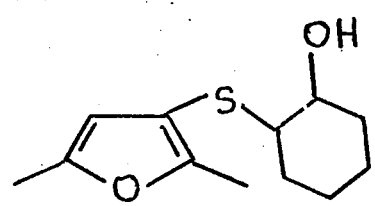

A test tube equipped with a magnetic stirrer is immersed in a water bath. Into the test tube are charged 1 ml of methanol, 4 drops of diethyl amine, 20 drops of 2,5-dimethyl-3-furanthiol, and 12 drops of cyclohexene oxide. The reaction mass is heated and stirred on a hot plate at about 60°C for 2 hours. The reaction mass is then concentrated in vacuo on a rotary evaporator. The product is isolated by preparative GLC (Conditions: 8 feet × ¼ inch 25% SE-30 column; 120°C programmed at 6°C/min).

Mass spectral, infrared and NMR analyses confirm the structure as being:

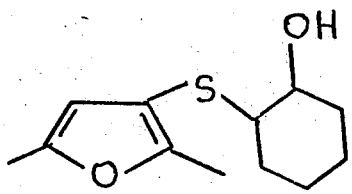

Mass spectral analysis is as follows:

| m/e | |
|---|---|
| 226 parent ion | 41 |
| 128 | 81 |
| 43 | 28 |
| 95 | |

This material has a meaty, pork and yeast character.

EXAMPLE XIV (2-hydroxy cyclohexyl) (2-methyl-3-furyl) sulfide prepared according to the process of Example XII is added to a 2% solution of Wyler's "Beef Flavored Instant Bouillon" (manufactured by Wyler Foods, Division of Borden, Inc., Chicago, Il., U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 0.1 ppm. This chemical adds a bacon characteristic to the beef broth.

EXAMPLE XV (2,5-dimethyl-3-furyl) (2-hydroxy cyclohexyl) sulfide prepared according to the process of Example XII is added to a 2% solution of Wyler's "Beef Flavored Instant Bouillon" (manufactured by Wyler Foods, Division of Borden, Inc., Chicago, Il., U.S.A.).

(Ingredients: salt, hydrolyzed vegetable protein, malto dextrin, sugar, beef fat, water, monosodium glutamate, flavorings, corn sugar, beef extract, caramel color, hydrogenated vegetable fat, U.S. certified food color)

at the rate of 0.2 ppm. This chemical adds a cooked pork note to the beef broth.

What is claimed is:

1. A 3-furyl beta-chalcogenalkyl sulfide having the structure:

wherein X is a chalcogen selected from the group consisting of oxygen and sulfur; $R_2$ and $R_3$ are each selected from the group consisting of methyl and hydrogen, at least one of $R_2$ or $R_3$ being methyl and hydrogen, at least one of $R_2$ or $R_3$ being methyl; and $R_4$ and $R_5$, taken separately, are each methyl.

2. The 3-furyl beta-chalcogenalkyl sulfide compound of claim 1 wherein X is sulfur.

3. The 3-furyl beta-chalcogenalkyl sulfide compound of claim 1 wherein X is oxygen.

4. The 3-furyl beta-chalcogenalkyl sulfide compound of claim 2 wherein $R_2$ is methyl, $R_3$ is hydrogen, and $R_4$ and $R_5$ is each methyl.

5. The 3-furyl beta-chalcogenalkyl sulfide compound of claim 3 wherein $R_2$ is methyl, $R_3$ is hydrogen and $R_4$ and $R_5$ is each methyl.

6. The 3-furyl beta-chalcogenalkyl sulfide compound of claim 2 wherein $R_2$, $R_3$, $R_4$ and $R_5$ is each methyl.

7. The 3-furyl beta-chalcogenalkyl sulfide compound of claim 3 wherein $R_2$, $R_3$, $R_4$ and $R_5$ is each methyl.

* * * * *